United States Patent [19]

Biehl

[11] Patent Number: 5,419,309
[45] Date of Patent: May 30, 1995

[54] TIP CLEANING ACCESSORY FOR RIGID ENDOSCOPIC INSTRUMENT

[76] Inventor: Albert G. Biehl, 1116 Highland Bch. Dr., Highland Beach, Fla. 33487

[21] Appl. No.: 836,409

[22] Filed: Feb. 18, 1992

[51] Int. Cl.[6] .............................................. A61B 1/00
[52] U.S. Cl. ...................................................... 128/4
[58] Field of Search ................ 128/4; 134/169 C, 182

[56] References Cited

U.S. PATENT DOCUMENTS

| | | | |
|---|---|---|---|
| 4,991,565 | 2/1991 | Takahashi et al. | 128/4 |
| 5,025,778 | 6/1991 | Silverstein et al. | 128/4 |

Primary Examiner—Richard J. Apley
Assistant Examiner—Beverly A. Meindl

[57] ABSTRACT

A tip cleaning accessory for enhancement in the utility of rigid endoscopic instruments is hereinafter disclosed. This accessory includes a complimentary tubular member adapted for use with a rigid endoscope. The endoscope contemplated for use with such an accessory includes a handset or handle, a rigid tubular shaft, having a plurality of functional channels adapted for acceptance of at least two fiber optic bundles, the first bundle for illuminating the operative field and a second bundle for visualization of the operative field, either directly through an eye piece (located within the instrument handset) or upon a video screen by coupling a video camera to the imaging bundle. The tip cleaning accessory of this invention comprises an adaptive and complimentary tubular member for use in conjunction with the endoscope to provide and direct a source of cleansing fluid to the tip of the endoscope so as to enable removal of debris from the optical windows associated with both the light and imaging bundles of the instrument. This accessory can be supplied along with new endoscopic instruments and is also compatible with endoscopic instruments of existing design.

2 Claims, 3 Drawing Sheets

TIP CLEANING ACCESSORY FOR RIGID ENDOSCOPIC INSTRUMENT

BACKGROUND OF THE INVENTION

1. Field of the Invention

This invention is directed to an apparatus and to a method. More specifically, this invention is directed to a tip cleaning accessory for endoscopic instruments, the combination thereof with an endoscopic instrument and to a method for removal of fluids and other debris from the tip of an endoscopic instrument—specifically the optical windows associated with the tip of the endoscopic instrument.

2. Description of the Prior Art

Endoscopic instruments can generally be classified into two distinctive categories: the so-called "flexible" class of instruments (represented by sigmoidscopes); and, the so-called "rigid" class of endoscopic instruments (represented by cystacope, arthroscope and laproscopes). Each genera or class of instrument is unique unto itself, both in respect to design and operation; and, such differences are related to the specific and highly specialized uses for which each has been designed.

The rigid endoscope is generally designed for both diagnosis (biopsy) and for performance of surgical procedures utilizing what has become to be known as "least invasive surgical" techniques and procedures (or LIS). In accordance with such techniques, a small incision is made into the abdomen (laparoscopic procedure) or joint (arthroscopic procedure), the instrument introduced through such incision into the patients body by means of a trokar and a surgical procedure performed. Typically, the endoscope is provided with a series of internal channels to allow for introduction of one or more accessories (snares, electrodes and micro-surgical devices) into the patients body; and, means for illumination and visualization of the operative field. It is also possible to provide for aspiration and suction of an irrigant to and from the operative field through internal channels provided for such purpose. Under certain conditions it may be necessary or appropriate to use one or more endoscopes in combination to effect the desired surgical procedure.

As is evident from the foregoing, the limited size of the incision into the patient's body precludes direct observation of the operative field by the surgeon and, thus, the surgeon must rely upon the visual access provided by the instrument to effect the operative procedure. Traditional visual access to the operative field has been provided through a combination of fiber optic bundles incorporated into the endoscope; one such fiber optic bundle optically coupled to a light source and a second fiber optic bundle optically coupled to an eye piece or video camera. Each of the fiber optic bundles are shielded or capped at the end of the endoscope with a window which can become obscured with blood, fecal matter, bodily fluids and/or tissue fragments in the course of the performance of a surgical procedure. In such event, the instrument need be withdrawn, the tip of the endoscope cleaned of obscuring matter and reinserted. This interruption of the surgical procedure both prolongs the surgical procedure and subjects the patient to additional risk. Accordingly, there is a continuing need to provide for enhancement of existing endoscopic instruments to minimize and/or avoid the limitations thereupon imposed by current design.

OBJECTS OF THE INVENTION

It is the object of this invention to remedy the above as well as related deficiencies in the prior art.

More specifically, it is the principal object of this invention to provide an accessory for use in conjunction with rigid endoscopic instruments of existing design to effect removal of obscuring debris from the tip thereof to ensure continuity of observation of the operative field through the fiber optics bundles of the endoscope provided for that purpose.

It is another object of this invention to provide an accessory for use in conjunction with rigid endoscopic instruments of existing design to deliver a stream of cleansing fluid to the tip of the endoscopic instruments for removal of obscuring matter.

It is yet another object of this invention to provide a method for delivery of the cleansing fluid to the tip of the endoscopic instrument in the course of performance of a surgical procedure so as to avoid interruption thereof.

SUMMARY OF THE INVENTION

The above and related objects are achieved by providing a tip cleaning accessory for an endoscopic instrument which includes a tubular member having a cylindrical wall, an instrument channel having a defined size and shape which conforms in overall dimension to the cross-sectional area and length of an endoscopic instrument; a fluid channel running the length of the tubular member, said fluid channel being associated with and-/or incorporated into the cylindrical wall thereof; means associated with one end of the fluid channel for fluid coupling to a source of cleansing fluid; and, means associated with the opposite end thereof for directing cleansing fluid onto the tip of the endoscope associated therewith to effect removal of blood, fecal matter, bodily fluids and/or tissue debris from the optical window associated with the instrument so as to preserve essentially unobstructed optical coupling of the light and imaging fiber optics bundles (associated with the endoscope) and the operative field.

In one of the preferred embodiments of the invention, the end of the tip cleaning accessory (which is physically associated with the tip of the endoscope) is provided with one or more nozzles of jets for directing cleansing fluid onto the tip of the endoscope.

In another of the preferred embodiments of the invention, indexing means are associated with the tubular member to permit and/or to effect alignment of the nozzles or jets of the tubular member with the optical window in the tip of the endoscopic instrument.

DESCRIPTION OF THE INVENTION INCLUDING PREFERRED EMBODIMENTS

Figure 1A:
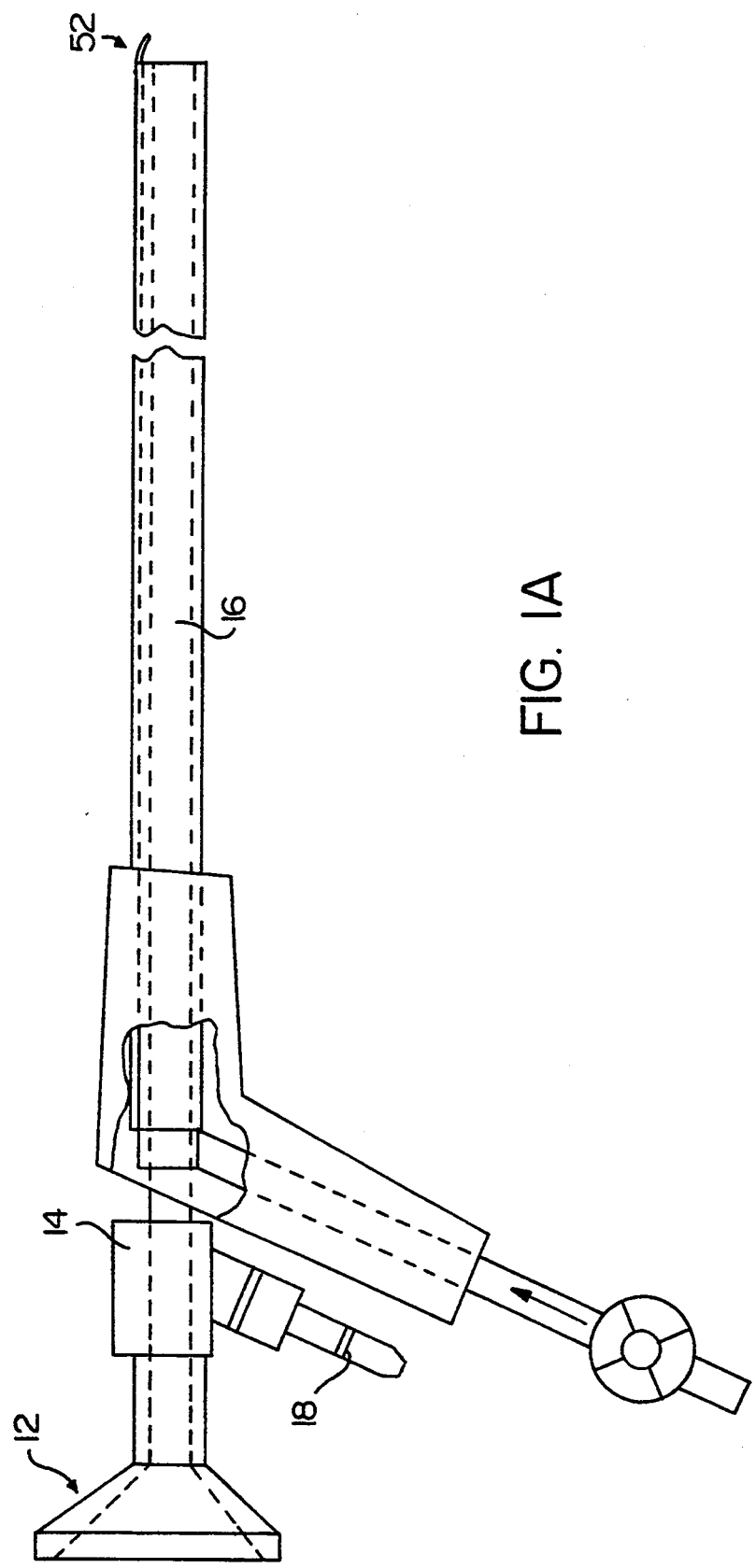
FIG. 1(a) is a perspective view of an endoscope in combination with a unique cleaning accessory

The preferred embodiments of this invention are, for ease of description and understanding, described in reference to one or more of the accompanying figures.

Where an element or component is common to more than one of these figures, it is assigned a common reference numeral to aid in understanding and to provide continuity in description.

Figure 1B:
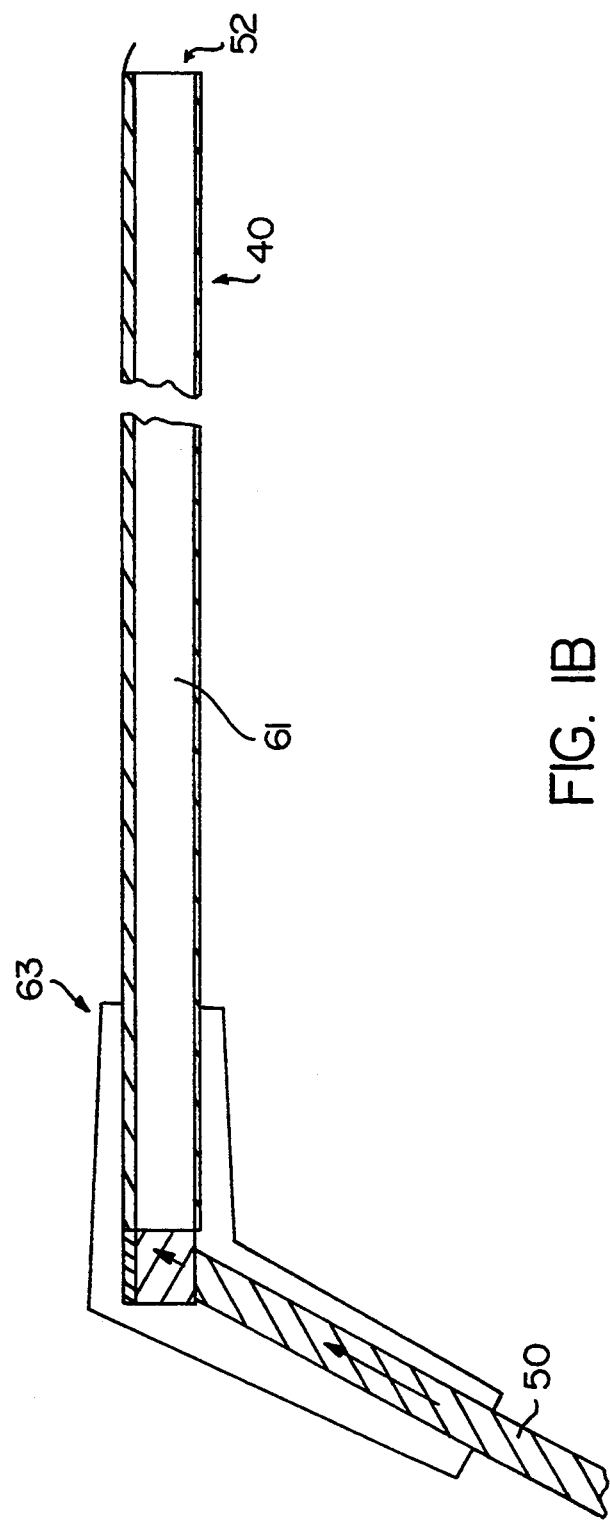
FIG. 1(b) is a cross-sectional view of the cleaning accessory shown in FIG. 1(a).

FIG. 1 depicts, in perspective view, an endoscopic instrument of traditional design in combination with the cleaning accessory of tiffs invention. In brief, such endoscopic instrument includes an eyepiece (12) to which is connected an optical train (not shown) which permits the clinician to observe the operative field through a fiber optic bundle or imaging bundle which extends from the handset (14) through a shaft (16) to the area of surgical interest. In addition to the imaging bundle, a second fiber optic bundle or light carrier (18) is also provided. The light carrier is connected through the hand set to a light source which illuminates the operative field, thereby permitting its visualization through the imaging bundle. In addition to the fiber optic bundles or elements, additional channels can be provided through the shaft for various accessories and surgical instruments (i.e. electrodes, snares, and micro surgical devices).

In the conventional instrument design of the type described in FIG. 1, the shaft can be provided with additional passageways to permit the aspiration, or infusion, of an irrigant in the operative field and removal of such irrigant either through the same channel or through a separate channel provided for that purpose. In practice, the infusion, sequential or concurrent, with suction of an irrigant into the operative field may, under certain conditions, assist in clearing debris from the window (20) which seals the fiber optic elements within the shaft, thus preventing direct contact of fluid therewith. Where an endoscopic instrument does, in fact, make provision for such internal irrigation and suction channel, the utility of the instrument is somewhat limited due to the fact that the overall cross-sectional area of such instrument is limited (both by custom and practice) to approximately 10-12 min. Accordingly, it is preferable to eliminate such internal irrigation channel in favor of additional accessory channels or elimination thereof in favor of a instrument of smaller cross-sectional area.

In rite smaller diameter instruments, and in older instruments, which are lacking in such irrigation, the aspiration and suction of an irrigant is not generally possible through the same endoscope which is used to perform the operative procedure; thus, necessitating a second incision and a second endoscope to perform the irrigation and suction functions. Where this latter protocol is prevalent, the irrigant cannot effectively clean the optical window through which the imaging and light bundles rely for access to the operative field.

Figure 2:
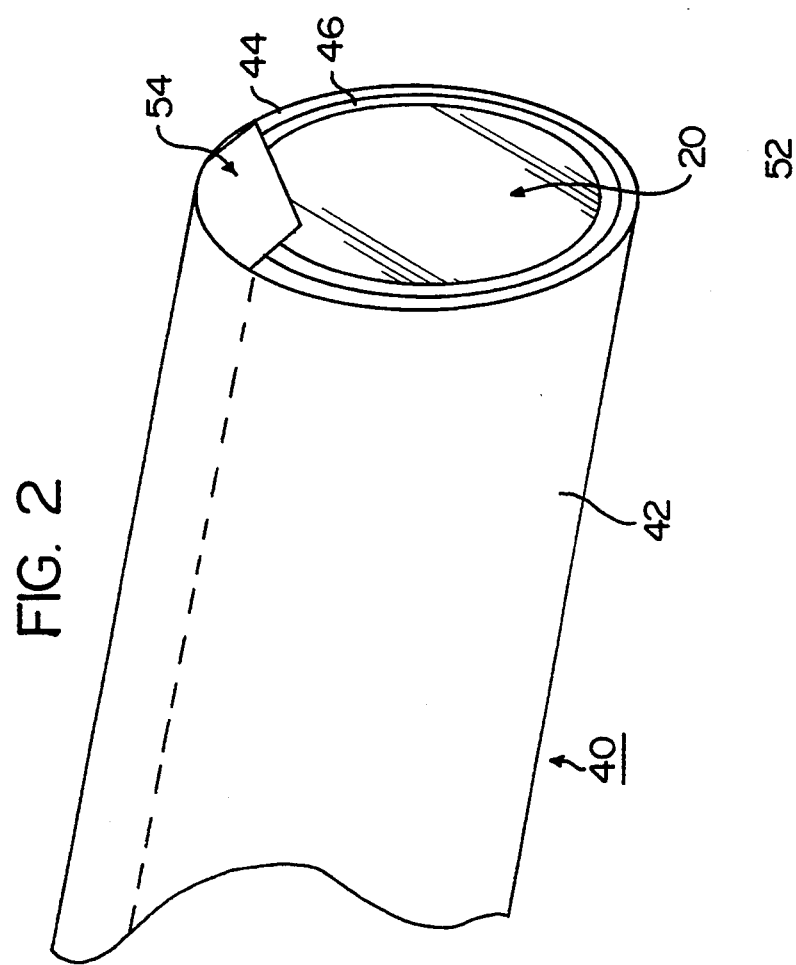
FIG. 2 is an enlarged view of the distal portion of the cleaning accessory.

In accordance with this invention, a tip cleaning accessory is herein provided as shown in FIG. 2. This tip cleaning accessory (40) comprises (in the embodiment shown), a tubular member (42) comprising two concentric tubes (44, 46), one of which is somewhat smaller in diameter than the other. These two tubes are joined together at their respective ends so as to provide a channel therebetween (48) for infusion of an irrigant or cleaning fluid from a source external to the operative field to the tip of the endoscopic instrument associated therewith. In practice, the endoscopic instrument is inserted, or nested within the tip cleaning accessory and the resulting assembly inserted in the conventional manner through a trokar positioned in the abdominal cavity of the patient. In order to present a pressurized operating environment, (as is requisite in laparoscopic surgery wherein the abdominal cavity is distended by pressurization thereof with an inert gas), the distal end (52) of the instrument channel (61) of the tip cleaning accessory is preferably provided with means for sealing engagement (62) of the distal end of such channel (52) and the distal end of the instrument shaft (16). The tip cleaning accessory is and remains in passive engagement with the endoscopic instrument until such time as the tip of the instrument becomes obstructed by materials which adhere to the optical window covering the imaging fiber optic bundles. At that time, the clinician simply energizes a pump (not shown) which forces irrigant (generally saline or other equivalent fluid) through an inlet (50) provided in the proximal end of the tip cleaning accessory. Fluid passes through the channel (48) provided in the tip cleaning accessory from the inlet (50) to the distal end or the tip of the cleaning accessory (52) where it is deflected by one or more nozzles or jets (54) onto the window (20) which covers the channel housing the fiber optic elements. The frequency and amount of irrigant deflected onto the window at the tip of the fiber optic channel is carefully controlled by the clinician and can be removed from the operative field through a suction channel provided for that purpose either in the tip cleaning accessory or by simply reversing the flow of fluid through the tip cleaning accessory by means of suction applied to the proximal end of the tip cleaning accessory.

Figure 3:
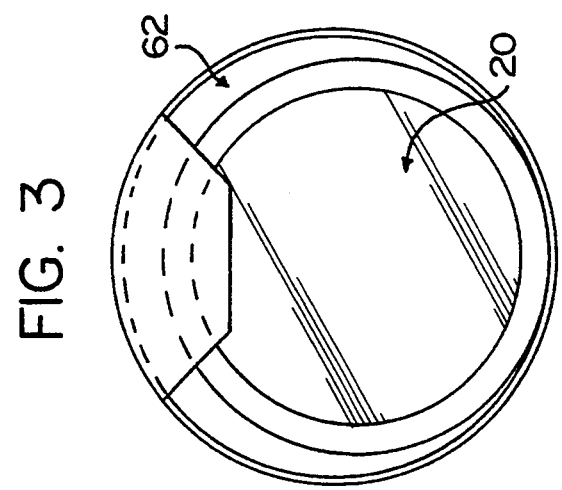
FIG. 3 is an end view of the distal portion of the cleaning accessory.

In the preferred embodiment of this invention as illustrated in FIG. 3, the tip cleaning accessory is provided with a series of jets (54) integral with the distal end thereof, which is associated with the tip of the endoscope shaft. The endoscope shaft and the tip of the cleaning accessory are further provided with an index mark or detente (63) which assures the orientation of the jets in the tip cleaning accessory relative to the window which covers the fiber optic bundle channel and thereby assuring accurate and directive placement of cleansing fluid relative to the optical window at the tip of the endoscopic instrument.

As is apparent to one skilled in the art, the foregoing figures are simply illustrative of the concept of this invention and not intended as delineating in scope which is set forth in the following claims.

What is claimed is:

1. A tip cleaning accessory for use in conjunction with an endoscopic instrument, said endoscopic instrument having a rigid shaft that is essentially circular in cross-section and further characterized as having (i) means for optical coupling of a light source and a viewing means with a handset; (ii) a handset for control and manipulation of said endoscopic instrument and (iii) an essentially rigid shaft mechanically coupled to said handset comprising a plurality of channels which run the length thereof, including at least one channel for a fiber optic element which channel is sealed by a transparent window on the distal end thereof, said accessory comprising:

(a) a cylindrical tubular member of composite construction having, in combination,
(i) a cleansing fluid channel defined by a first hollow, essentially cylindrical tubular member or casing, characterized as having an open proximal end and an open distal end and a second hollow, essentially cylindrical tubular member, or sleeve, characterized as having an open proximal end and an open distal end, each of said first and second tubular member being essentially equivalent in overall length and joined to the other at the proximal and distal ends thereof so as to form a continuous fluid channel along a common interface of said first and second tubular member, said fluid channel being further characterized as having one or more fluid discharge jets formed in the distal end thereof and (ii) an endoscopic instrument receiving channel defined by the hollow, essentially cylindrical sleeve of said tubular member;

(b) means for fluid coupling of the cleansing fluid channel of said tubular member to a source of cleansing fluid; and, (c) means for sealing engagement of the distal end of said tubular member with an endoscopic instrument at the distal end of said instrument, upon insertion of the shaft of said instrument into the instrument receiving channel of the hollow sleeve of the tubular member, so as to form a fluid impervious barrier between said member and said instrument (d) means, including at least one nozzle or jet, for directing a cleansing fluid discharged from the cleansing fluid channel of said tubular member onto a transparent window at the distal end of said endoscopic instrument so as to effectively remove debris from said transparent window; and (e) indexing means on both of said tubular member and said endoscopic instrument to assure effective orientation of said fluid directing means and said transparent window upon insertion and rotation of the shaft of said instrument into the instrument receiving channel.

2. In an endoscopic instrument devoid of internal means for delivery a cleansing fluid to a transparent window on the distal end thereof, said instrument having a rigid shaft that is essentially circular in cross-section and further characterized as comprising (i) means for coupling at the proximal end thereof, a light source and/or viewing means with a handset; (ii) a handset for control and manipulation of said endoscopic instrument; (iii) an essentially rigid shaft coupled to said handset and extending therefrom, said rigid shaft having a plurality of channels running the length thereof, including at least one channel for a fiber optic bundle, which channel is sealed with a transparent window at the distal end thereof, wherein the improvement comprises:

(a) a cylindrical tubular member of composite construction having, in combination, (i) a cleansing fluid channel defined by a first hollow, essentially cylindrical tubular member, or casing, characterized as having an open proximal end and an open distal end and a second hollow, essentially cylindrical tubular member, or sleeve, characterized as having an open proximal end and an open distal end, each of said first and second tubular member being essentially equivalent in overall length and joined to the other at the proximal and distal ends thereof so as to form a continuous fluid channel along a common interface of said first and second tubular member, said fluid channel being further characterized as having one or more fluid discharge jets formed in the distal end thereof and (ii) an endoscopic instrument receiving channel defined by the hollow, essentially cylindrical sleeve of said tubular member;

(b) means for fluid coupling of the cleansing fluid channel of said tubular member to a source of cleansing fluid; and, (c) means for sealing engagement of the distal end of said tubular member with an endoscopic instrument at the distal end of said instrument, upon insertion of the shaft of said instrument into the instrument receiving channel of the hollow sleeve of the tubular member, so as to form a fluid impervious barrier between said member and said instrument;

(d) means, including at least one nozzle or jet, for directing a cleansing fluid discharged from the cleansing fluid channel of said tubular member onto a transparent window at the distal end of said endoscopic instrument so as to effectively remove debris from said transparent window; and (e) indexing means on both of said tubular member and said endoscopic instrument to assure effective orientation of said fluid directing means and said transparent window upon insertion and rotation of the shaft of said instrument into the instrument receiving channel.

* * * * *